United States Patent [19]

Osterburg et al.

[11] Patent Number: 4,943,354
[45] Date of Patent: Jul. 24, 1990

[54] PROCESS FOR THE CONTINUOUS SEPARATION OF WATER FROM METHYL TERT-BUTYL ETHER MIXTURES

[75] Inventors: Günther Osterburg, Rheurdt; Milan Prezelj, Frankfurt am Main, both of Fed. Rep. of Germany

[73] Assignee: Deutsche Texaco Aktiengesellschaft, Hamburg, Fed. Rep. of Germany

[21] Appl. No.: 326,493

[22] Filed: Mar. 17, 1989

Related U.S. Application Data

[63] Continuation of Ser. No. 17,664, Feb. 24, 1987, abandoned.

[30] Foreign Application Priority Data

Feb. 26, 1986 [DE] Fed. Rep. of Germany ....... 3606121

[51] Int. Cl.$^5$ ............................................. C07C 41/42
[52] U.S. Cl. ...................................... 203/14; 203/39; 203/DIG. 19; 568/699
[58] Field of Search ................... 203/14, DIG. 19, 99, 203/39, 23, 98, 52, 68, 70; 568/699, 697

[56] References Cited

U.S. PATENT DOCUMENTS

| | | |
|---|---|---|
| 2,854,385 | 9/1958 | Alheritiere ............................. 203/16 |
| 3,404,175 | 10/1968 | Mercier ................................. 568/699 |
| 3,640,851 | 2/1972 | Mourier ....................... 203/DIG. 19 |
| 3,738,915 | 6/1973 | DiFore et al. ......................... 203/14 |
| 4,302,298 | 11/1981 | Mikitenko et al. .................. 568/699 |
| 4,490,563 | 12/1984 | Van Pool et al. ..................... 203/14 |
| 4,518,462 | 5/1985 | Aoshima et al. ...................... 203/39 |
| 4,544,776 | 10/1985 | Osterburg et al. ......... 203/DIG. 19 |

*Primary Examiner*—Wilbur Bascomb
*Attorney, Agent, or Firm*—Vincent A. Mallare; Thomas H. Whaley

[57] ABSTRACT

An energy saving process for purification of methyl tertbutyl ether by fractional distillation of a mixture containing dissolved water and $C_4$ hydrocarbons characterized by phase separation of water and methyl tertiary butyl ether within the distillation column and withdrawal of the separated water phase from the column at a point below the point at which the mixture is supplied to the column.

1 Claim, 1 Drawing Sheet

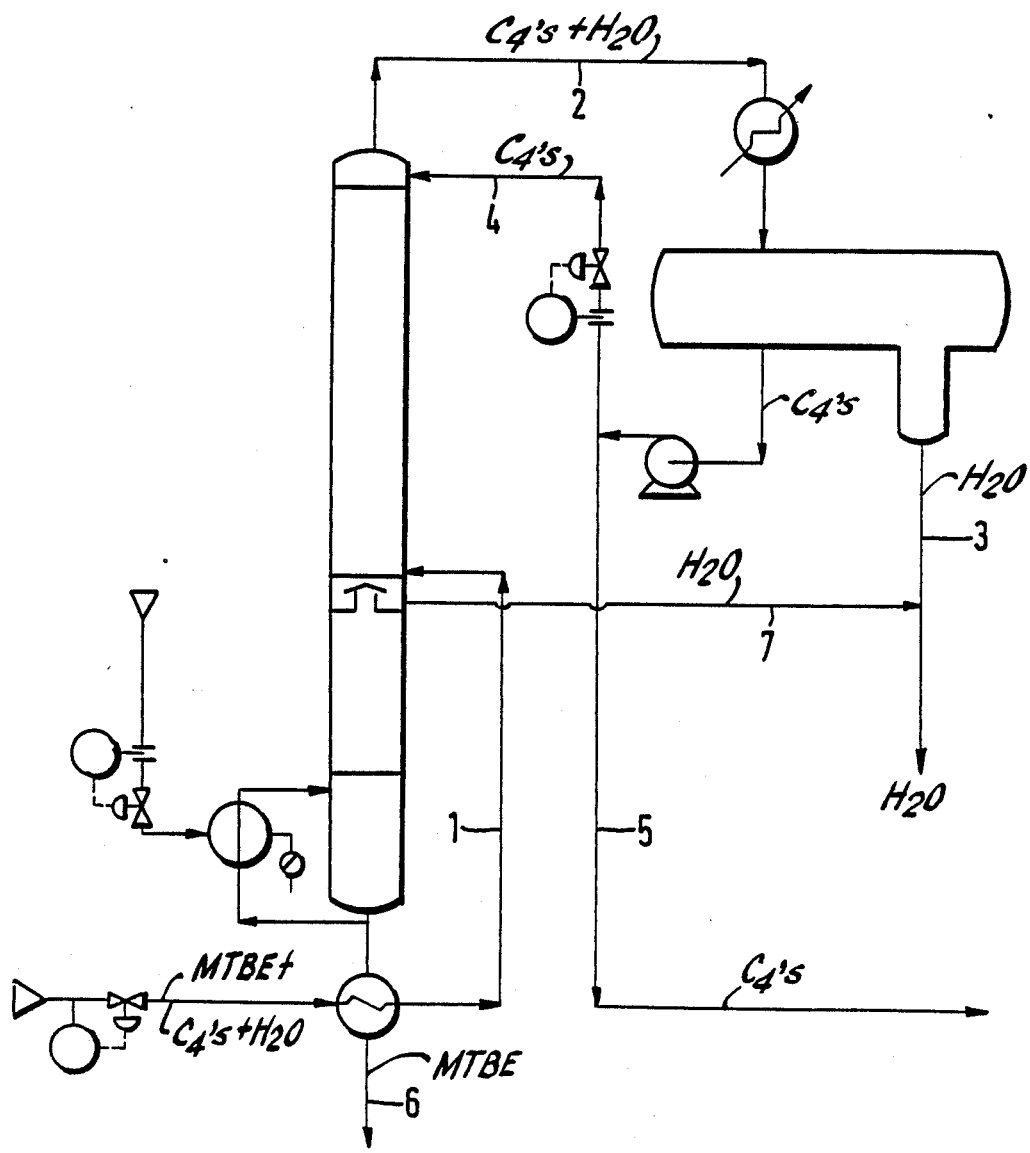

4,943,354

PROCESS FOR THE CONTINUOUS SEPARATION OF WATER FROM METHYL TERT-BUTYL ETHER MIXTURES

This is a continuation of application Ser. No. 17,664, filed Feb. 24, 1987 now abandoned.

BACKGROUND OF THE INVENTION

1. Field of the Invention

This invention relates to a process for the continuous separation of water during distillative purification or splitting-up of organic substances or mixtures of substances in a distillation column which contain water in a dissolved form, the organic substances or mixtures of substances having only limited capability of absorbing water and, with water boiling as azeotropes, or without the capability of forming azeotropes with water, boiling higher than water.

It is known that in the distillative splitting-up of mixtures of substances the presence of water involves considerable separation problems. This is particularly true if one of the components of the materials mixture is a solubilizer for water.

Such solubilizers for water are usually the products contained in the distillation feed and to be purified during distillative separation. Solubilizers for water, are for instance, methyl tert-butyl ether, methyl ethyl ketone and sec-butyl alcohol.

Disclosure Statement

German Patent DE-OS 25 47 380, discloses a reaction product of the methyl tert-butyl ether (MTBE) synthesis which contains, besides $C_4$-hydrocarbons, mainly MTBE and unreacted methanol and minor quantities of tert-butyl alcohol (TBA) and dimethylether (DME) is first subjected to washing with water in order to eliminate methanol. Thereby, due to solubilization of MTBE, water is transferred to the raffinate phase of the extractor that has been freed from methanol by washing. The water content in this raffinate phase is dependent on the MTBE concentration which, in its turn, is dependent on the isobutene concentration in the $C_4$-cut feedstock for the MTBE synthesis. At low isobutene concentrations, small amounts of MTBE are formed which, thus, solubilize only little water into the raffinate phase. This water, together with the relatively great quantity of inert $C_4$-hydrocarbons, can be easily phased out azeotropically and withdrawn and can be separated when the latter products are separated from MTBE. At high isobutene concentrations, however, correspondingly great quantities of MTBE are formed which solubilize so much water into the raffinate phase that this may possibly be no longer sufficiently phased out azeotropically together with the amount of inert $C_4$-hydrocarbons during separation from MTBE. In this case, sufficient elimination of water can only be attained by correspondingly higher vaporization of $C_4$-hydrocarbons (higher refluxing), or subsequent drying of the formed MTBE is necessary.

German Patent DE-OS 23 47 097 discloses the production of methyl ethyl ketone (MEK) from water-containing sec-butyl alcohol (SBA), by dehydrogenation or by oxidation wherein more or less water-containing crude products are obtained. According to the process described in DE-OS 23 47 197, water contents of between 3 and 15 percent have to be expected. Expediently, such reaction products are first dried prior to isolation of MEK. Drying is usually done with azeotropic entraining agents such as benzene, hexane, cyclohexane, heptane.

U.S. Pat. No. 3,228,985, discloses a multistage process for purifying MEK in which the stream to be purified is first extractively distilled with sodium carbonate solution, is then treated with pentane while an aqueous phase is formed, and the residual water of the organic phase is azeotropically distilled off. The utilities consumption of such azeotropic drying operations is mainly determined by the composition of the ternary azeotropes and their decomposition into phases.

During conventional production of SBA (sec-butyl alcohol) by indirect hydration using, e.g., sulfuric acid as a catalyst, a watercontaining crude alcohol is obtained.

Patent Specifications GB-PS 829 424, DE-OS 1 017 602, and DE-OS 2 033 707 disclose distillation procedures for the purification of aqueous crude SBA. In these processes, the water contained in the crude alcohol is jointly separated with higher-boiling byproducts or impurities in a separating column. Formation of azeotropes with water is then a basic prerequisite for the separability of byproducts or contaminants such as di-sec-butyl ether (DSBE) and $C_8$-hydrocarbons from SBA. On the other hand, the water contained in the crude SBA, which itself forms an SBA-rich homogeneous azeotrope with SBA, can be separated with such byproducts from SBA without too great quantities of SBA being phased out with the water from the SBA to be purified. A dry SBA is obtained.

Therefore, from the composition of the ternary azeotropic mixture thus formed and the solubility product resulting from this heterogeneous ternary composition, the following alternative conditions for the distillation are inferred: either a sufficient amount of water for the separation of the amount of azeotropically higher-boiling byproducts entrained in the distillation or a sufficient amount of azeotropically higher-boiling by-products for the separation of the amount of water entrained in the distillation has to be made available.

Patent Specification GB-PS 829 424 particularly describes the problem of how, during the distillation of aqueous crude SBA, the water and azeotropically higher-boiling by-products can be separated in a column by controlled refluxing of aqueous phase and organic phase from the overhead product separator while maintaining a stable equilibrium in the column.

These examples make clear that the separation of water from such or similar product systems always involves a considerable effort with respect to the apparatuses or the utilities consumption.

German Patent Specification 24 07 949 outlines the formation of binary and/or ternary azeotropic mixtures is usually made use of and it is unavoidable to perform the operation with reflux ratios adjusted to the removal of water, to use separate drying columns, or to carry out drying with a molecular sieve in the sidestream of the column.

Therefore, it is an object of the present invention to develop easily feasible or less expensive separation processes which are particularly capable of simultaneously separating by-products or contaminants and water.

SUMMARY OF THE INVENTION

According to the present invention, this problem of water separation is solved by effecting, under distillation conditions in the distillation column, the separation of water from the organic substances or mixtures of substances to be purified by utilizing the presence of one or more substances boiling overhead and reducing the solubility of water in the organic substances or mixtures of substances to be purified such that liquid water, wholly or in part, separate from the organic substance below the feed point and is withdrawn at the side of the distillation column.

Thus, the substance or the substances boiling overhead reduce the solubility of water in the organic substances of mixtures of substances to be purified, or form together with water only insufficient azeotropes and thus reduce the limit of solubility for water in the organic substances or mixtures of substances.

DESCRIPTION OF THE DRAWING

The FIGURE is a diagrammatic representation of distillation apparatus illustration the process this invention.

DETAILED DESCRIPTION OF THE INVENTION

The process relates to organic substances or mixtures of substances to be purified which have only limited capability of absorbing water. Due to the presence of one or more substances reducing the solubility water in the organic substances or mixtures of substances to be purified, the water is eliminated.

Preferred substances for limiting the solubility of water in the product MTBE are components of the product stream, e.g hydrocarbons, which decrease the solubility of water in the MTBE so that water is forced to separate from the mixture. The solubility limit for water in the product to be produced is reduced by the joint presence of high-boiling products in the distillation feed preventing or limiting the entraining of water into the overhead product. But products limiting the water solubility are also those products which are contained in a concentrated form in the high-boiling overhead product and which further reduce at a suitable point in the column (below the feed point) the solubility limit for water in the product to be produced. Such products are, for instance, n-hexane that lowers the solubility of water in methyl ethyl ketone and di-sec-butyl ether that lowers the solubility of water in sec-butyl alcohol.

According to the process of the present invention, a state of permanent water saturation is maintained in the column so that the water continuously entrained with the distillation feed is inevitably eliminated due to oversaturation and can be withdrawn nonvaporized.

After the separation of water in the column, the residual water content in the outflowing liquid column product is always lower than the possible water content in the ascending vaporous column product so that automatically a dry product is warranted at the column sump.

According to the invention, water is withdrawn from utilized for separating and withdrawing water in the distillation column below the feed point. Thus, formation of water azeotropes overhead of the column can be eliminated or the amount of water azeotropes overhead of the column can be lowered.

The residual water content in the liquid product stream flowing out to the stripping section of the column which results from the solution equilibrium at this water separation point, is azeotropically refluxed to the column section above the water separation point by the organic vapors formed by vaporization and ascending in the stripping section. For this return transport of water on the basis of the individually possible azeotropic compositions, a vaporization effort is necessary that mostly results from the separation task overlapping with the separation of other impurities. Thus, no additional vaporization effort is required for the separation of water.

In those cases where solely the separation of water is necessary, the vaporization effort has only to be adjusted to the entraining of water and to the azeotropic properties in the stripping section of the column by a correspondingly forced reflux to the column.

Moreover, also by deliberate and controlled water removal at the separating tray, the water concentration in the stripping section of the column can be adjusted and maintained as required for specific separation tasks.

Thus, it is possible to withdraw the water to be separated from water containing organic mixtures, wholly or in part, without additional or with a considerably lower vaporization effort, by means of a water separator located below the feeding point in the distillation column.

The technical realization of the principle of the invention can be achieved by boosting the efficiency of a distillation column which is particularly suitable for the azeotropic drying operation by an incorporated water separator. The water separator should be installed at the point where the highest water separation has to be expected. In any case, not higher than the feeding tray or shortly below.

In this connection, it is unimportant whether an external water separator outside the column or a water separating tray inside the column, is employed. The important thing is that all of the product outflowing to the stripping section of the distillation column is conducted via the water separator. By this means entraining of water into the stripping section of the column can always be adjusted by the solubility of water in the liquid product on the water separating tray, irrespective of the water concentration in the feedstock.

The following examples illustrate the invention. The examples show that by the process of the invention a significant reduction of the distillation effort for the separation of water is achieved or an additional distillation effort for the separation of water exceeding the actual separation task is avoided.

EXAMPLE 1

In a continuously operated distillation column schematically depicted in the FIGURE, a water-containing mixture of methyl tert-butyl ether (MTBE) and $C_4$-hydrocarbons at a ratio of 65:35 parts-by-weight was separated by distillation at a pressure of 6 bar. The feed mixture was fed via line 1 in the lower part of the column, 15 trays above the column sump.

Water entrained in the column was azeotropically phased out via line 2 together with the $C_4$-hydrocarbons as overhead product, was separated after condensation of the overhead product and was withdrawn from the reflux vessel via line 3. To keep up the separation of MTBE/$C_4$-hydrocarbons part of the overhead product was refluxed to the column via line 4. The overhead product portion contained in the feedstock was withdrawn as a distillate via line 5. The reflux ratio (R/D) for determining the utilities consumption during this distillation is calculated from the ratio of reflux (R) to distillate (D).

In the comparison tests 1.1 and 1.2 it is shown that when considering the simultaneous drying of water-containing feed mixtures, this reflux ratio has to be raised, in unfavorable cases, to a higher ratio than required for the separation of MTBE and $C_4$-hydrocarbons.

EXAMPLE 1.1 (COMPARISON)

With a water portion of 9.1 g entrained in 1260 g of feed mixture (equal to 0.72 wt.% water) 1280 g of $C_4$ overhead product with 9.70 wt.% water were distilled off from the column by a reflux of 860 g and a R/D reflux ratio of 2.0. From this overhead product, 9.0 g of water could be separated and withdrawn as a liquid phase. In the column sump 830 g of $C_4$-free MTBE with a water content of less than 0.03 wt.% were obtained via line 6.

EXAMPLE 1.2 (COMPARISON)

With a water portion of 8.5 g entrained in a 1260 g of feed mixture (equal to 0.67 wt.% water) 970 g of $C_4$ overhead product with 0.57 wt.% water were distilled off by a reflux of 540 g and a R/D reflux ratio of 1.2. From this overhead product, 5.5 g of water could be separated and withdrawn as a liquid phase. Due to the insufficient entraining power for water of the overhead product, 830 g of $C_4$-free MTBE with a water content of 0.7 wt.% were obtained in the column sump via line 6.

In contrast thereto, as schematically depicted in the FIGURE the following results can be obtained according to the invention by incorporating a water separator at a suitable point of the column below the feeding tray and by withdrawing water via line 7:

EXAMPLE 1.3 ACCORDING TO THE PRESENT INVENTION

With a water portion of 9.8 g entrained in a 1400 g of feed product (equal to 0.70 wt.% water) 740 g of $C_4$ overhead product with 0.51 wt.% water were distilled off by a reflux of 250 g and a R/D reflux ratio of 0.5. From this overhead product, 3.6 g of water could be separated and withdrawn as a liquid phase. At the water separator in the column, 6.1 g of water could be withdrawn through line 7. In the column sump, 910 g of $C_4$-free MTBE with a water content of less than 0.02 wt.%, were obtained through line 6.

EXAMPLE 1.4 (ACCORDING TO THE PRESENT INVENTION

With a water portion of 35 g entrained in 1400 g of feed product (equal to 2.4 wt.% water) 740 g of $C_4$ overhead product with 0.5 wt.% water were distilled off by a reflux of 250 g and a R/D reflux ratio of 0.5. From this overhead product, 3.7 g of water could be separated and withdrawn as a liquid phase. At the water separator in the column, 31.3 g of water could be withdrawn through line 7. In the column sump, 910 g of $C_4$-free MTBE, with a water content of less than 0.02 wt.%, were obtained through line 6.

We claim:

1. In a process for the separation of methyl tert-butyl ether from a mixture comprising methyl tert-butyl ether, water and $C_4$ hydrocarbons by fractional distillation in a distillation column having means for vaporization of liquid at the base of the column and means for condensing vapors passing overhead therefrom and for returning a portion of the resultant condensate to the top of the column as reflux, the improvement which comprises:
   (a) introducing a feed mixture comprising $C_4$ hydrocarbons and methyl tert-butyl ether containing dissolved water into the distillation column at a feed point intermediate the base and top of the column,
   (b) distilling $C_4$ hydrocarbon overhead with entrained water vapor,
   (c) condensing the distillate vapors with the formation of two immiscible liquid phases comprising a first water-rich phase and a $C_4$-rich phase,
   (d) returning a portion of the $C_4$-rich phase to the top of the column as reflux,
   (e) collecting a second water-rich phase and an immiscible methyl tert-butyl ether-rich phase at a point in the column below the feed point and above the base of the column,
   (f) withdrawing the second water-rich phase from the distillation column, and
   (g) recovering methyl tert-butyl ether substantially freed from dissolved water from the base of the column.

* * * * *